United States Patent [19]

Scott

[11] Patent Number: 4,467,038

[45] Date of Patent: Aug. 21, 1984

[54] PREDETECTOR RESERVOIR FOR CHROMATOGRAPHIC ANALYSIS INSTRUMENT

[75] Inventor: Richard L. Scott, Bartlesville, Okla.

[73] Assignee: Phillips Petroleum Company, Bartlesville, Okla.

[21] Appl. No.: 326,109

[22] Filed: Nov. 30, 1981

[51] Int. Cl.$^3$ .......................................... G01N 31/08
[52] U.S. Cl. ..................................... 436/115; 73/23.1; 422/80; 422/89; 436/123; 436/158; 436/161
[58] Field of Search ............... 436/115, 123, 133, 149, 436/151, 158, 160, 161; 422/78, 80, 89; 73/23.1

[56] References Cited

U.S. PATENT DOCUMENTS

| | | | |
|---|---|---|---|
| 3,304,159 | 2/1967 | Hinsrark | 23/230 |
| 3,518,059 | 6/1970 | Levy | 422/89 X |
| 3,524,305 | 8/1970 | Ives | 55/386 |
| 4,170,893 | 10/1979 | Kleiss | 73/23.1 |
| 4,173,145 | 11/1979 | Durbin | 73/422 GC |
| 4,234,315 | 11/1980 | Scott | 23/230 PC |
| 4,325,907 | 4/1982 | Dembicki, Jr. et al. | 422/89 X |

OTHER PUBLICATIONS

Schematic Diagrams (3 Pages) from User's Manual Provided by Designer of Chromatography Equipment Showing Typical Arrangements of Columns, Detectors and Valves.

Primary Examiner—Arnold Turk

[57] ABSTRACT

A gas chromatographic apparatus is provided which comprises a gas chromatography column, a detector and an extended conduit between the column and the detector, the conduit providing means for flow of a gas so as to enable essentially complete elution of the gas from the column before the gas is detected by the detector. The apparatus can be adapted for use in an instrument for the elemental analysis of a sample for carbon, hydrogen, nitrogen and sulfur. The invention method includes the steps of introducing a sample in vapor form into a gas chromatography column, passing the sample through the column so as to separate at least one component of interest, passing the component of interest through a conduit to the detector so as to reach the detector after the essentially complete elution of the component of interest from the column.

26 Claims, 2 Drawing Figures

PREDETECTOR RESERVOIR FOR CHROMATOGRAPHIC ANALYSIS INSTRUMENT

This invention relates to gas chromatography. In one aspect, the invention relates to improving the response linearity for a detection device in a gas chromatograph. In another aspect, the invention relates to an instrument for the analysis of carbon, hydrogen and nitrogen in a sample.

Instruments for the chemical analysis of a sample of matter often include a sampling means to inject a known size sample, a gas chromatography column for separation of the vaporized constituents of the sample, a detector which senses the presence of the constituents as they elute from the column, and a recovering device which records the response of the detector in a form, such as peaks on a chart, which is representative of the amount of each constituent. The constituents of the sample, in mixed vapor form, are swept through the column and in contact with the detector in an inert carrier gas. As a constituent gas elutes from the column, there is an increase in the gas flow rate due to the addition of the adsorbed phase to the normal flow of the carrier gas. This effect causes the eluting gas to pass the detector faster and differentially with respect to the portion of peak eluting at any given moment. The result is a nonlinear response for the detector over varying concentrations and consequent necessity of additional calibration points to determine the true shape of the calibration curve.

It is an object of the invention to provide an improved method and apparatus for chromatographic analysis of a sample of matter.

It is a further object of the invention to provide a means for compensating for the effect of increase in gas flow rate as a sample constituent elutes from a gas chromatography column.

It is a further object to provide an improved instrument for the measurement of carbon, hydrogen, nitrogen and sulfur in a sample.

SUMMARY OF THE INVENTION

According to the invention, a sample of matter is passed in gaseous form in an inert carrier gas through a gas chromatography column wherein the sample is separated into at least two components, at least one of which is passed to a detector via an extended conduit for reducing the nonlinearity of detector response as the component elutes from the column, the extended conduit having an effective volume, at the flow rate of the carrier gas, which is at least equal to the volume of the constituent to be detected by the detector plus the volume of the associated carrier gas. In a specific embodiment, a sample of matter is analyzed for its carbon, hydrogen, nitrogen and sulfur components by heating the sample in oxygen, passing the resulting mixture comprising carbon dioxide, water, sulfur dioxide and nitrogen in a carrier gas to a first gas chromatography column wherein the mixture is separated into its sulfur dioxide, water and unresolved carbon dioxide and nitrogen phases, passing the first column effluent to a first detector to determine a property of the effluent representative of its composition, passing the carbon dioxide and nitrogen eluting from the first detector to a second gas chromatography column wherein the carbon dioxide and nitrogen are further separated into a carbon dioxide phase and an unresolved nitrogen phase, passing the effluent from the second column through an extended conduit to a second detector for determination of a property representative of its composition, the extended conduit having an effective volume at least equal to the volume of the carbon dioxide to be detected by the detector plus the volume of the associated carrier gas, passing the nitrogen phase to a third column for separation of nitrogen, and passing the nitrogen eluting from the third column to a third detector.

Further according to the invention, apparatus for the chemical analysis of matter is provided which comprises a gas chromatography column, means for detecting a property of gas eluting from the gas chromatography column, and an extended conduit providing means for gas flow from the gas chromatography column to the detector, the extended conduit having an effective volume at least equal to the volume of the eluting gas plus the volume of the associated carrier. In a specific embodiment of the invention, apparatus is described which comprises a combustion chamber, a first gas chromatography column, a first detector, a second gas chromatography column, a second detector, means for fluid flow from each element to the next, the means for fluid flow between at least one of the gas chromatography columns and its respective detector being an extended conduit having an effective volume at least equal to the volume of the constituent to be detected by the detector.

The invention offers the advantages of requiring fewer samples to determine the profile of a calibration curve of detector response, simplifying automatic determination of sample content, and permitting greater accuracy of sample analysis.

DETAILED DESCRIPTION OF THE INVENTION

The invention apparatus includes a gas chromatography column for the separation of constituents of a gaseous mixture. Any gas chromatography column effective for such separation is suitable for the invention apparatus and method.

The invention apparatus includes a detector which is sensitive to a property of a fluid which is representative of its composition. Any suitable detection system can be used, including a wheatstone bridge detection network. Suitable detectors include thermal conductivity, infrared and fluorescent detectors.

The invention apparatus also includes a predetector reservoir which comprises an extended conduit for fluid flow from the outlet end of the gas chromatography column to the detector. The extended length of the conduit reduces the effect on the detector of peak elution from the column and improves detector response linearity. The conduit is preferably open, i.e., not packed with a solid material. The conduit may be any suitable material which is inert to the chemicals being analyzed, such as stainless steel, Teflon ® and glass.

Stainless steel is the preferred material for the predetector reservoir.

The dimensions of the predetector reservoir can vary widely depending upon the nature of the instrument and the analysis being performed. The length of the extended conduit is that length which is effective under the instrument conditions, including carrier gas flow rate, temperature and detector type, to reduce the effect on detector linearity of a gas eluting from the gas chromatography column. In general, the dimensions of the predetector reservoir must be such that the internal volume of the conduit is sufficient to retain the volume of the fluid to be detected plus its associated carrier gas. Thus, the volume of the conduit will be at least that which will permit the fluid of interest to completely elute from the column prior to its initial detection by the detector.

Figure 1:
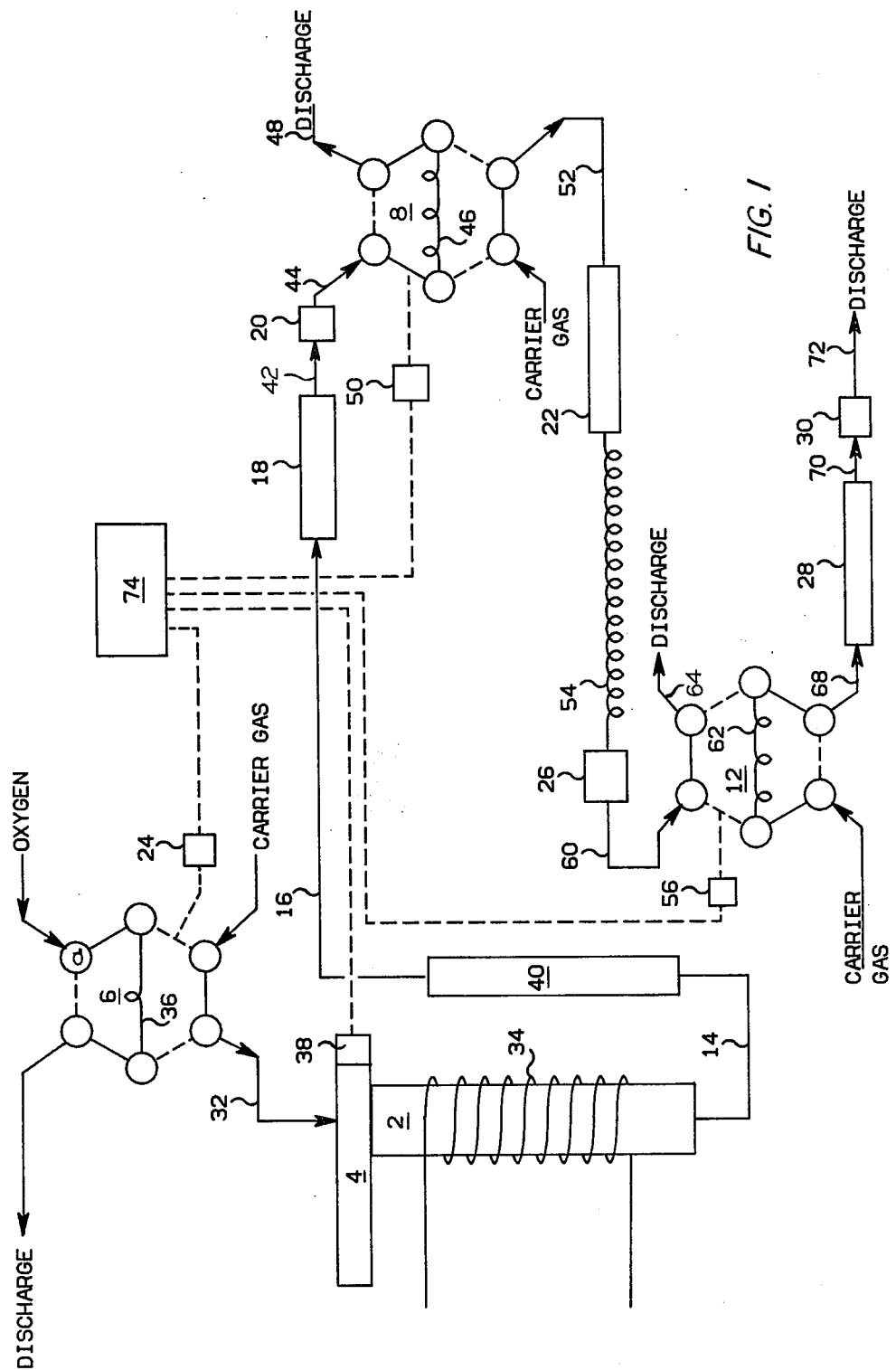
FIG. 1 is a schematic representation of a carbon, hydrogen, nitrogen and sulfur analyzer employing the invention predetector reservoir.

The use of the invention predetector reservoir in an analytical instrument can best be described by reference to FIG. 1. Shown schematically in FIG. 1 is a gas chromatography instrument for the quantititative analysis of a sample for carbon, hydrogen, nitrogen and sulfur. In the illustrated instrument, a sample of a material to be analyzed is introduced into combustion chamber 2 through sample introduction means 4. An inert carrier gas such as helium or argon is introduced from a source (not shown) into combustion chamber 2 via sample introduction means 4, conduit means 32 and valve means 6. Valve means 6, 8 and 12 are schematically shown as a multi-port, multi-conduit valves as described in U.S. Pat. Nos. 3,111,849 and 4,234,315. The valves can also be double-seated solenoid equivalents of such 6-port valves. The positions of valves 6, 8 and 12 can be controlled automatically by programmable timing means 74 and actuating means 24, 38, 50 and 56 as are known in the art of chromatographic analysis.

Sample introduction means 4 can be a conventional indexing sample holder provided with suitable means for sealing the passage between the sample holder and the combustion chamber and between conduit means 32 and the sample holder.

Combustion chamber 2 is heated by coil 34. A measured volume of oxygen in loop 36 is supplied via port 6-a at a suitable pressure to the combustion chamber. The oxygen is swept into the combustion chamber 2 by the carrier gas. The combustion chamber is maintained at a temperature effective for rapid, essentially complete combustion of the sample, generally about 1025° C.

The combustion products, which include carbon dioxide, sulfur oxides, water and nitrogen, are swept by the carrier gas via conduit 14 through reduction chamber 40, which can be copper at a temperature of about 825°–900° C., for reduction of any $SO_3$ present to $SO_2$, consumption of excess oxygen, and reduction of nitrogen oxides. Conduit 14 is preferably a glass tube having a volume of about 30 cc maintained at 200°–300° C. to insure sulfuric acid dissociation.

The products of combustion are swept from reduction chamber 40 through conduit 16 into the first chromatographic column 18. The gaseous mixture entering the column includes carbon dioxide, water, nitrogen and sulfur dioxide. The first chromatographic column 18 functions to separate the gaseous mixture into water vapor, sulfur dioxide, and an unresolved phase containing carbon dioxide, nitrogen and the remaining constituents of the reaction mixture. Colume 18 can be of any suitable material and packing. Column 18 is preferably 22'×9 mm (o.d.) glass tubing packed with Floropak-80 coated with 20 m Carbowax and about 20 inches of Poropak S at about 120° C. Water and sulfur dioxide can be vented via discharge line 48.

Effluent from the first column 18 is passed via connecting means 42 to first detector means 20. Connecting means 42 is generally a small-volume (1 cc or less) conduit. Detector means 20, and also detector means 26 and 30, can be conventional means for detecting a property of a fluid mixture which is representative of the composition of the fluid mixture. Detector means 20 can be a thermal conductivity detector. Such a detector provides signals representative of the difference in thermal conductivity between the column effluent and the carrier gas. The temperature difference between the resistance elements can be measured by an electrical bridge circuit, such as a wheatstone bridge. However, detector means 20 can be any other type of device for measuring a property of a gaseous stream representative of its composition, including infrared and fluorescent detectors. Detector means 20, 26 and 30 are preferably, in the system shown, thermal conductivity detectors.

Effluent from detection means 20 is passed via conduit 44 to valve 8 and into delay means 46. Conduit 44 is preferably ⅛" tubing 1–2 feet in length. Delay means 46, and likewise delay means 62, can be a piece of tubing with dimensions suitable for achieving a desired delay time. The delay means are designed to permit the effluents of interest to be retained in the system until the entire peak can be switched to another column. This type of system is described in U.S. Pat. No. 4,234,315 issued to Richard L. Scott on Nov. 18, 1980, the disclosure of which is hereby incorporated by reference. In the instrument shown the delay means are ⅛" steel tubing about 54 feet in length. With proper timing of the 6-port valve 8, water and sulfur dioxide separated on the first column 18 are vented via discharge conduit 48 and the remaining mixed gases are passed to second chromatographic column 22 via conduit 52. Conduit 52 is preferably ⅛" steel tubing 1–2 feet in length.

Second chromatographic column 22 functions to separate carbon dioxide and, if present, any halogens, nitrogen oxides, ammonia and hydrogen sulfide, from the remaining unanalyzed components of the reaction product mixture to provide a carbon dioxide peak and an unresolved nitrogen peak. Column 22 can be of any suitable materials and packing. Column 22 is preferably packed with porous polymer, such as Porapak T, and maintained at a temperature of 60°–80° C.

In general in such an analysis system, the volume of carbon dioxide is quite high in comparison with the other components of the combustion product mixture. The relatively large volume of $CO_2$ results in an increase in flow rate and a loss of detector linearity which is particularly pronounced. FIG. 1 illustrates a system in which the invention predetector reservoir 54 extends from the outlet of column 22 directly to the inlet of detector 26. The effluent from column 22 is swept by the carrier gas into predetector reservoir 54, the volume of which is such that the carbon dioxide peak will have completely eluted from the column before it is detected by detector 26.

In general, the volume of the predetector reservoir employed in the invention is at least sufficient to retain the entirety of the component of the column effluent which is to be detected by the detector. Thus, the effluent of interest will have substantially completely eluted from the column into the reservoir before that effluent is detected by the detector. If, for example, the detector response is being recorded in the form of peaks on a chart, the constituent of interest will have completely eluted from the column before the detection, and thus the charting, of that peak has begun. The volume can generally be described as the flow rate volume of the carrier gas multiplied by the time of elution of the largest peak. Such treatment of the effluent compensates for the increase in flow rate across the detector as a peak elutes from the column.

The reservoir is preferably, in order to prevent undesired gas turbulence and diffusion, an open, extended conduit of relatively great length compared to inner diameter. In analysis systems such as that shown in FIG. 1, the predetector reservoir will generally be a coiled tube having an inner diameter in the range of about $\frac{1}{2}$-1/10 inch, preferably about $\frac{1}{8}$-$\frac{3}{8}$ inch. Suitable tubing has been found to be $\frac{1}{4}$ inch (o.d.) stainless steel.

The length of the predetector column will vary depending upon the flow rate of the carrier gas and the elution time from the column. One skilled in the art of chromatography can determine the minimum dimensions of such a predetector column by, for example, noting the time necessary for the constituent of interest to elute from the column used and applying the formula $L=(4RT/\pi D^2)$, in which L is the length of the predetector reservoir in cm, D is the inside diameter of the predetector reservoir in cm, R is the rate of carrier gas flow in ml/min, and T is the time for peak elution. In the system illustrated in FIG. 1, a suitable length for $\frac{1}{4}$ inch (o.d.) stainless steel tubing with a helium carrier gas flow rate of about 85 cc/min is about 50 feet. It would not be unusual in such an analyzer for the predetector reservoir to exceed 28 feet in length. Such an instrument is commonly used to analyze solid samples as large as 6-15 mg. If the column effluent contains more than one constituent of interest, the predetector reservoir must be sufficiently long to accomodate the constituent having the greater volume. If a major peak follows the peak of interest, the peaks should be a sufficient distance apart that the peak of interest has passed through the detector before the next major peak enters the predetector reservoir.

Referring again to FIG. 1, effluent from second column 22 passes via predetector reservoir 54 to detector 26, which detects and emits a signal representative of the presence of carbon dioxide and an unresolved nitrogen mixture. The carbon dioxide eluting from column 22 is not detected until it has substantially completely eluted from the column.

The effluent from detector 26 passes via conduit 60, multi-port valve 12, loop 62 and conduit 68 to third gas chromatography column 28. Conduit 60 is preferably $\frac{1}{8}$ inch stainless steel tubing about 1-2 feet in length. Carbon dioxide is vented from the system in valve 12 via discharge line 64. The remaining mixed effluent is passed via conduit 68, a $\frac{1}{8}$-inch connecting line about 1-2 feet in length, into third gas chromatography column 28.

Third gas chromatography column 28 functions to separate nitrogen from the remaining combustion products. Column 28 can contain any suitable packing. Satisfactory results have been obtained with a column packed with 13X molecular sieve material maintained at a temperature of about 70°-80° C. Effluent from column 28 is passed via connecting means 70, which is generally a small-volume (1 cc or less) conduit, to third detector 30. Detector 30 generates a signal representative of the presence of nitrogen. The gases passing from detector 30 are discharged via discharge line 72.

Variations of the instrument shown in FIG. 1 are possible. For example, the location of the invention predetector reservoir will be downstream of a gas chromatography column, between the column outlet and the detector inlet. The predetector reservoir of the illustrated system is positioned downstream of the second column because of the large volume of the carbon dioxide peak which elutes; however, use of the detector precolumn with either or both of the other detectors would be desirable under other analysis conditions.

EXAMPLE

This example is provided to illustrate the lack of response linearity resulting from flow rate changes as a peak elutes from a gas chromatography column, and to show the improvement in detector response linearity with the invention system.

An instrument essentially as shown schematically in FIG. 1 was used to analyze known amounts of the substances listed, with amounts of each, in Table I.

TABLE I

| Sample | Weight (mg) | Point |
|---|---|---|
| Acetanilide | 2.733 | 1 |
|  | 3.929 | 4 |
| NBS sulfur | 3.358 | 2 |
| standard 1623* | 4.000 | 5 |
|  | 4.168 | 17 |
|  | 5.019 | 18 |
| Hexamethylbenzene | 4.588 | 3 |
|  | 4.491 | 8 |
|  | 3.973 | 15 |
|  | 2.912 | 16 |
| Sulfanilamide in | 3.551 | 6 |
| graphite | 2.962 | 7 |
|  | 0.732 | 9 |
|  | 4.23 | 10 |
|  | 2.596 | 11 |
|  | 0.1744 | 12 |
|  | 0.6629 | 13 |
|  | 0.4036 | 14 |

*0.268% sulfur

Figure 2:
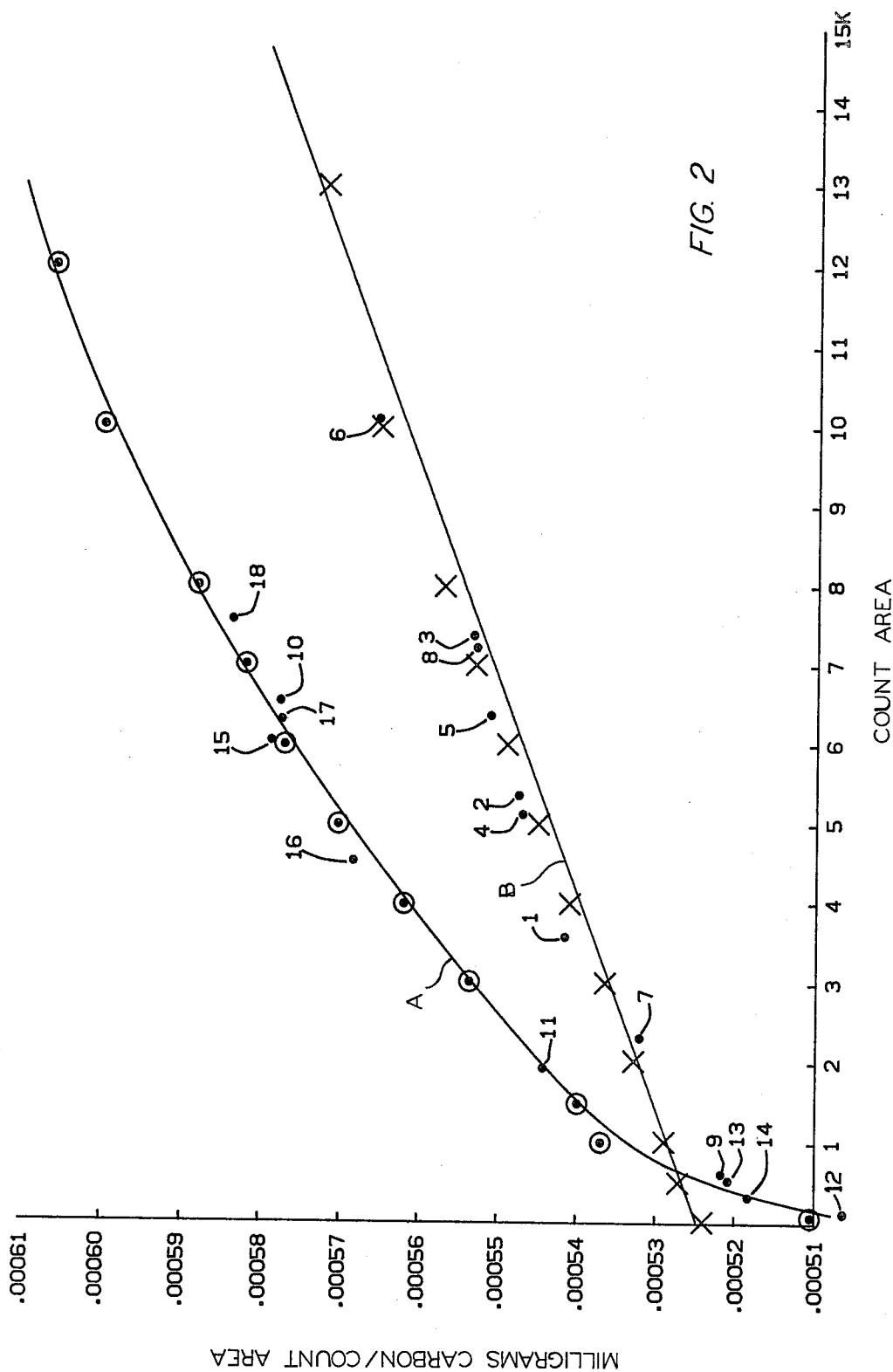
FIG. 2 is a calibration plot for carbon analysis using a thermal conductivity detector, Curve A representing analytical values obtained with the prior art instrument and Curve B representing a calibration curve obtained using the invention instrument.

The detector responses obtained are shown in FIG. 2, which is a graphical representation of milligrams of carbon per count area vs. count area. Ideally in such a plot, the peak area (represented as counts) should vary directly with milligrams of carbon per count, resulting in a linear plot.

The instrument used was a CHNS analyzer using helium carrier at a flow rate of 10 lbs on a steel ball with a Mathison 600 series rotometer. The combustion chamber was maintained at a temperature of about 1025° C. Helium carrier gas was introduced into the combustion chamber at a rate of 20 cc/min. The combustion products were swept from the combustion chamber to the first column, packed with Carbowax and Porapak S. The temperature of the first column was about 120° to 130° C. This first column separated nitrogen and carbon dioxide from sulfur and hydrogen, the latter two being read by a thermoconductivity cell in association with a recorder.

The nitrogen and $CO_2$ were passed to a second gas chromatograph column packed with Porapak T and maintained at a temperature of about 70°-80° C., and the eluting gases were passed to a second thermal conductivity detector. FIG. 2 is a plot of this detector response (in mg C/count area) versus count area. The effluent from the second detector was passed to a third chromatographic column, packed with a mole sieve and maintained at a temperature of about 70°–80° C., then passed to a third thermal conductivity detector.

Curve A of FIG. 2 is a best-fit calibration curve obtained from analyses of various compounds in standard samples by the described CHNS instrument which was not equipped with the invention predetector reservoir while Curve B is a best-fit calibration curve from analysis of various compounds in standard samples obtained using the CHNS instrument equipped with about fifty feet of quarter-inch (o.d.) stainless steel tubing extending from the outlet of the second column to the inlet of the second detector. The lack of linearity of Curve A makes accurate determination of the concentration of an unknown sample impossible by extrapolation from a limited number of known samples. By contrast, Curve B could be used to extrapolate the concentration of an unknown sample with significantly greater accuracy.

I claim:

1. Apparatus for determination of a property of a constituent of a sample in mixed vapor form in a carrier gas introduced into the apparatus at a rate R, the apparatus comprising:
   a gas chromatographic column having an inlet end and an outlet end;
   a detector for detecting a property of the constituent of sample related to its composition, the detector having an inlet end and an outlet end;
   conduit means between the outlet end of the gas chromatography column and the inlet end of the detector for flow of the constituent of the sample, the conduit means directly connecting the gas chromatography column with the detector, said conduit means having an effective volume, at the rate of carrier gas flow, at least sufficient to contain the constituent to be detected plus the volume of the associated carrier gas.

2. The apparatus of claim 1 in which the volume of the conduit means is represented by the formula $V=RT$, where R is the flow rate of the carrier gas in cc/min and T is the time in minutes for the elution of the constituent of the sample.

3. The apparatus of claim 1 in which the conduit means is an open tube having an inner diameter D and the length L of the conduit is represented by the formula $L=4RT/\pi D^2$, where R is the rate of carrier gas flow in ml/min and T is the time in minutes for the constituent to elute from the column.

4. The apparatus of claim 1 in which the conduit means is an open tube having an inner diameter in the range of about 1/10 to about ½ inch.

5. The apparatus of claim 4 in which the conduit means is an open tube having an inner diameter in the range of about ⅛ to about ⅜ inch.

6. The apparatus of claim 4 further comprising means defining a combustion zone for volatilization of a solid sample to produce a combustion product in flow communication with the inlet end of the gas chromatography column.

7. The apparatus of claim 6 further comprising means defining a reduction zone for chemical reduction of at least one constituent of the combustion product having an inlet end in flow communication with the means defining the combustion zone and an outlet end in flow communication with the inlet end of the gas chromatography column.

8. The apparatus of claim 7 in which the detector is a thermal conductivity detector.

9. The apparatus of claim 8 in which the conduit means has an inner diameter of about ⅛ to about ⅜ inch.

10. An analytical instrument for the determination of at least the elemental carbon, hydrogen and nitrogen in a sample, comprising:
    means defining a combustion chamber having means for sample introduction, means for oxygen gas introduction, means for introduction of an inert carrier gas at a flow rate R and means for heating the sample to a temperature effective for essentially complete combustion of the sample to produce a mixed combustion product;
    gas chromatographic means for separating the mixed combustion product into a water phase, a sulfur dioxide phase, a carbon dioxide phase and a nitrogen phase;
    detector means for detecting a respective representative property of the water, the sulfur dioxide, the carbon dioxide and the nitrogen; and
    conduit means for fluid flow between the outlet end of a selected gas chromatographic means and the inlet end of a selected detector means, the conduit means directly connecting the gas chromatography column with the detector, said conduit means having an effective volume, at the rate of carrier gas flow, at least sufficient to contain the phase having the greatest volume which is being detected by the selected detector means.

11. The analytical instrument of claim 10 in which the conduit means is an open tube having an inner diameter D which is within the range of about 1/10 to about ½ inch and a length L which is at least $4RT/\pi D^2$, in which R is the carrier gas flow rate and T is the time of elution of the phase having the greatest volume which is being detected by the selected detector means.

12. The analytical instrument of claim 11 in which the conduit means is an open tube having an inner diameter of about ⅛ to about ⅜ inch.

13. The analytical instrument of claim 12 comprising a first gas chromatographic column to separate the sulfur dioxide phase in flow communication with a first detector to detect the presence of sulfur dioxide,
    a second gas chromatographic column to separate the carbon dioxide phase in flow communication with a detector to detect the presence of carbon dioxide, and
    a third gas chromatographic column to separate the nitrogen phase in flow communication with a third detector to detect the presence of nitrogen.
    the conduit means extending between at least one of the first, second and third chromatographic columns and its respective detector.

14. The analytical instrument of claim 13 further comprising means defining a reduction zone for chemical reduction of at least one constituent of the mixed combustion product between the means defining the combustion zone and one of the first, second and third gas chromatography columns.

15. The analytical instrument of claim 14 in which the detectors are thermal conductivity detectors.

16. The analytical instrument of claim 13 in which the conduit means extends between the second gas chromatographic column and the second detector.

17. The analytical instrument of claim 16 in which the second detector is a thermal conductivity detector.

18. The analytical instrument of claim 17 in which the conduit means is at least about 28 feet in length.

19. The analytical instrument of claim 18 which further comprises means operatively connected to the first, second and third detectors to produce a chromatogram of the respective detector responses.

20. A method for chemical analysis of a sample in an instrument comprising a gas chromatography column having an inlet end and an outlet end and a detector having an inlet end and an outlet end, comprising the steps of:
   (a) introducing at least a portion of the sample in the form of a mixture of gases into the inlet end of the gas chromatography column and passing the mixture of gases through the column in a carrier gas having a flow rate R so as to separate at least one component of interest from the mixture of gases;
   (b) passing the component of interest into a conduit directly extending from the outlet end of the gas chromatography column to the inlet end of the detector said conduit having an effective volume, at the rate of carrier gas flow, at least sufficient to contain the constituent to be detected plus the volume of associated carrier gas;
   (c) passing the component of interest through the conduit in the carrier gas having the flow rate R;
   (d) passing the component of interest to the inlet end of the detector after the essentially complete elution of the component of interest from the gas chromatography column; and
   (e) detecting a property of the component of interest.

21. The method of claim 20 in which the conduit is an open tube having a volume of at least RT, wherein R is the carrier gas flow rate in cc/min and T is the time for elution of the component of interest from the column.

22. The method of claim 20 in which the conduit is an open tube having an inner diameter D of about 1/10 to about ½ inch and a length L of at least $4RT/\pi D^2$, wherein R is the carrier gas flow rate in cc/min and T is the time for elution of the component of interest from the column.

23. The method of claim 22 in which the conduit is an open tube having an inner diameter of about ⅛ to about ⅜ inch.

24. The method of claim 21 which further comprises introducing a solid into a combustion zone and reacting the solid with a known volume of oxygen at a temperature at least sufficient to volatilize the solid and produce said sample in the form of a mixture of gases.

25. The method of claim 24 which further comprises passing the mixed gases through a reduction zone for chemical reduction of at least one component prior to introduction of the mixture of gases into the column.

26. The method of claim 25 which further comprises
   passing the mixed gases in the carrier gas to a first gas chromatography column for resolution of at least a water phase and a sulfur dioxide phase;
   passing at least the unresolved portion of the mixed gases to a second gas chromatography column for resolution of at least a carbon dioxide phase; and
   passing at least a further unresolved portion of the mixed gases to a third chromatography column for resolution of a nitrogen phase.

* * * * *